(12) United States Patent
Ohara et al.

(10) Patent No.: US 6,206,824 B1
(45) Date of Patent: Mar. 27, 2001

(54) FLEXIBLE TUBE FOR ENDOSCOPE AND METHOD OF PRODUCING THE FLEXIBLE TUBE

(75) Inventors: Kenichi Ohara, Gunma; Yoshinori Shibata; Hiromichi Shibuya, both of Tokyo; Hitoshi Hirose, Saitama; Kikuo Iwasaka, Saitama; Tatsuo Kubota, Saitama; Masaya Sato, Saitama; Tadashi Kasai, Saitama, all of (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/271,154

(22) Filed: Mar. 17, 1999

(30) Foreign Application Priority Data

Mar. 18, 1998 (JP) .................................................. 10-067545

(51) Int. Cl.[7] .................................................. A61B 1/00
(52) U.S. Cl. .................. 600/139; 600/140; 604/524; 604/526; 604/527
(58) Field of Search .................................. 600/139, 140; 604/524, 526, 527

(56) References Cited

U.S. PATENT DOCUMENTS

| 4,676,229 | * | 6/1987 | Krasnicki et al. | 128/4 |
| 4,753,222 | * | 6/1988 | Morishita | 128/4 |
| 4,944,287 | | 7/1990 | Takahashi et al. . | |
| 5,005,755 | | 4/1991 | Takahashi et al. . | |
| 5,529,820 | * | 6/1996 | Nomi et al. | 428/364 |
| 5,643,174 | * | 7/1997 | Yamamoto et al. | 600/114 |
| 5,873,866 | * | 2/1999 | Kondo et al. | 604/280 |
| 5,885,207 | * | 3/1999 | Iwasaka | 600/139 |
| 5,885,209 | * | 3/1999 | Green | 600/153 |

FOREIGN PATENT DOCUMENTS 2-51601   2/1984 (JP) .

* cited by examiner

*Primary Examiner*—Linda C. M. Dvorak
*Assistant Examiner*—Jocelyn Ram
(74) *Attorney, Agent, or Firm*—Greenblum & Bernstein, P.L.C.

(57) ABSTRACT

A flexible tube for an endoscope includes a spiral coil 11 as the innermost layer and a jacket 13 that is formed by applying a melt of a jacket material 1 and then curing it, in which the jacket material 1 has been allowed to penetrate through the gaps between adjacent turns of the innermost spiral coil 11 to reach the portion of its inner surface.

12 Claims, 7 Drawing Sheets

FIG. 7
PRIOR ART

FLEXIBLE TUBE FOR ENDOSCOPE AND METHOD OF PRODUCING THE FLEXIBLE TUBE

The Present disclosure relates to the subject matter contained in Japanese Patent Application No. Hei. 10-67545 filed on Mar. 18, 1998 which is expressly incorporated herein by reference in its entirety.

BACKGROUND OF THE INVENTION

1. Field of the Invention

The present invention relates to a flexible tube for an endoscope used as an inserting part of an endoscope. The present invention also relates to a method of producing the flexible tube.

2. Description of the Related Art

Flexible tubes for an endoscope are generally formed in such a manner that a spiral coil having one or more superposed layers are covered with a reticulate tube, which in turn is covered with a flexible jacket. The flexible jacket is formed by either of covering a flexible tube material therewith or applying a molten thermoplastic synthetic resin material on the reticulate tube and curing the applied layer.

Figure 6:
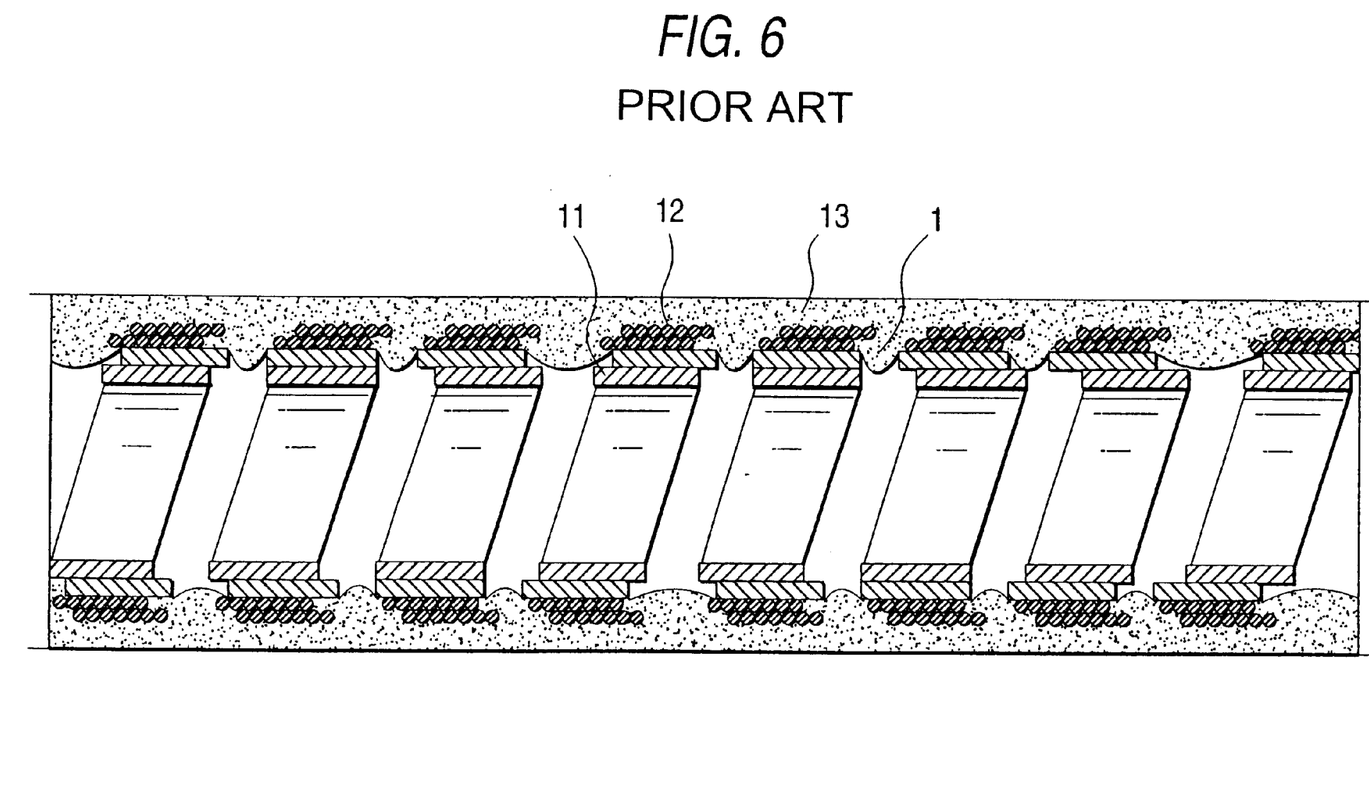
FIG. 6 is a partial longitudinal section of a conventional flexible tube for the endoscope.

FIG. 6 shows a conventional flexible tube for the endoscope, which has a jacket 13 formed by first applying a molten thermoplastic synthetic resin material and then curing the applied layer. Obviously, a jacket material 1 has penetrated through openings in the reticulate tube 12 to bind the jacket 13 and the reticulate tube 12. A reference numeral 11 represents a spiral coil 11.

However, a combination between the spiral coil 11 and the reticulate tube 12 is so weak that as the result of repeat use of the endoscope, gaps form between the two members 11 and 12 and the flexible tube becomes increasingly soft to introduce difficulty in inserting the endoscope into a body cavity.

Figure 7:
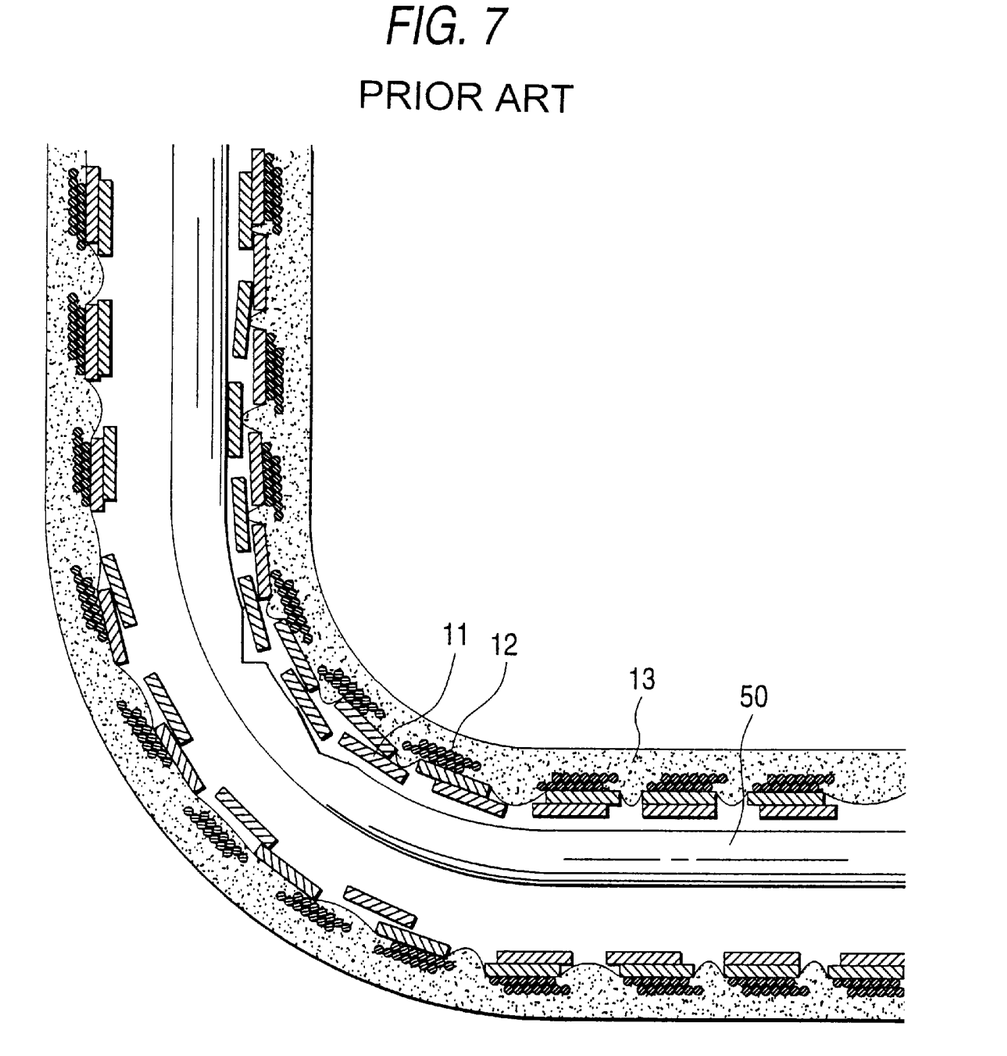
FIG. 7 shows in partial longitudinal section a bent portion of the conventional flexible tube for the endoscope.

Another problem in the conventional flexible tube for the endoscope is shown in FIG. 7. When using the flexible tube, the flexible tube bends in various directions at small radii of curvature or reverts to a straight form. As a result, a silicone rubber tube covering a bundle of optical fibers 50 passing through the flexible tube is damaged by inner edges of the spiral coil 11, often causing the internal optical fibers to break and become deteriorated in optical performance.

SUMMARY OF THE INVENTION

An object, therefore, of the present invention is to solve the aforementioned problems and to provide a flexible tube for an endoscope, which can be repeatedly used while an inner surface of an innermost spiral coil does not damage an internally passing optical fiber bundle and the like and the flexible tube hardly varies in flexibility.

Another object of the invention is to provide a method of producing the flexible tube for the endoscope.

According to a first aspect of the present invention, there is provided a flexible tube for an endoscope comprising:

a spiral coil defining gaps between adjacent turns of said spiral coil; and a jacket formed by a jacket material and covering at least an outer surface of said spiral coil;

wherein said jacket material penetrates through said gaps to cover at least edges of said spiral coil.

According to a second aspect of the present invention, there is provided the flexible tube as described in the first aspect of the present invention, wherein said spiral coil includes one or more superposed layers which are covered with one or more layers of a reticulate tube, and said reticulate tube is embedded in said jacket material.

According to a third aspect of the present invention, there is provided the flexible tube as described in the first aspect of the present invention, wherein the inner surface of said spiral coil is entirely covered with said jacket material.

According to a fourth aspect of the present invention, there is provided a method of producing a flexible tube for an endoscope comprising the steps of:

setting a spiral coil as an innermost layer on a mandrel with a clearance between an outer surface of said mandrel and an inner surface of said spiral coil;

applying a melt of a jacket material onto said spiral coil to penetrate through gaps between adjacent turns of said spiral coil into said clearance;

curing said jacket material; and removing said mandrel.

According to a fifth aspect of the present invention, there is provided the method as described in the fourth aspect of the present invention, wherein said spiral coil contains one or more superposed layers.

According to a sixth aspect of the present invention, there is provided the method as described in the fourth aspect of the present invention, further comprising the step of:

covering said spiral coil with one or more layers of a reticulate tube after setting said spiral coil.

According to a seventh aspect of the present invention, there is provided a method as described in the fourth aspect of the present invention, wherein said jacket material is a thermoplastic synthetic resin and applied with an extrusion molding machine.

According to an eighth aspect of the present invention, there is provided a method as described in the fourth aspect of the present invention, further comprising the step of:

conducting a bond enhancing treatment to members to which said jacket material is applied before applying said jacket material onto said spiral coil.

According to a ninth aspect of the present invention, there is provided a method as described in the fourth aspect of the present invention, wherein said members are said spiral coil and a reticulate tube.

According to the present invention, the jacket material that is cured after being applied in a molten state is allowed to penetrate through gaps between adjacent layers of the spiral coil as the innermost layer until it reaches the portions of the inner surface of the spiral coil. Therefore, the inner edges of the spiral coil can be covered with the jacket material. Hence, the flexible tube for the endoscope of the present invention permits a repeat use of an endoscope without causing the internally passing optical fiber bundle and the like to be damaged by the inner surface of the innermost spiral coil. If the inner surface of the spiral coil are all or in part covered with the penetration of the jacket material, the bond between the spiral coil and other member is sufficiently enhanced to reduce the variations in flexibility that will occur after the repeat use of the endoscope.

DETAILED DESCRIPTION OF THE PRESENT INVENTION

The present invention will now be described with reference to accompanying drawings.

Figure 1:
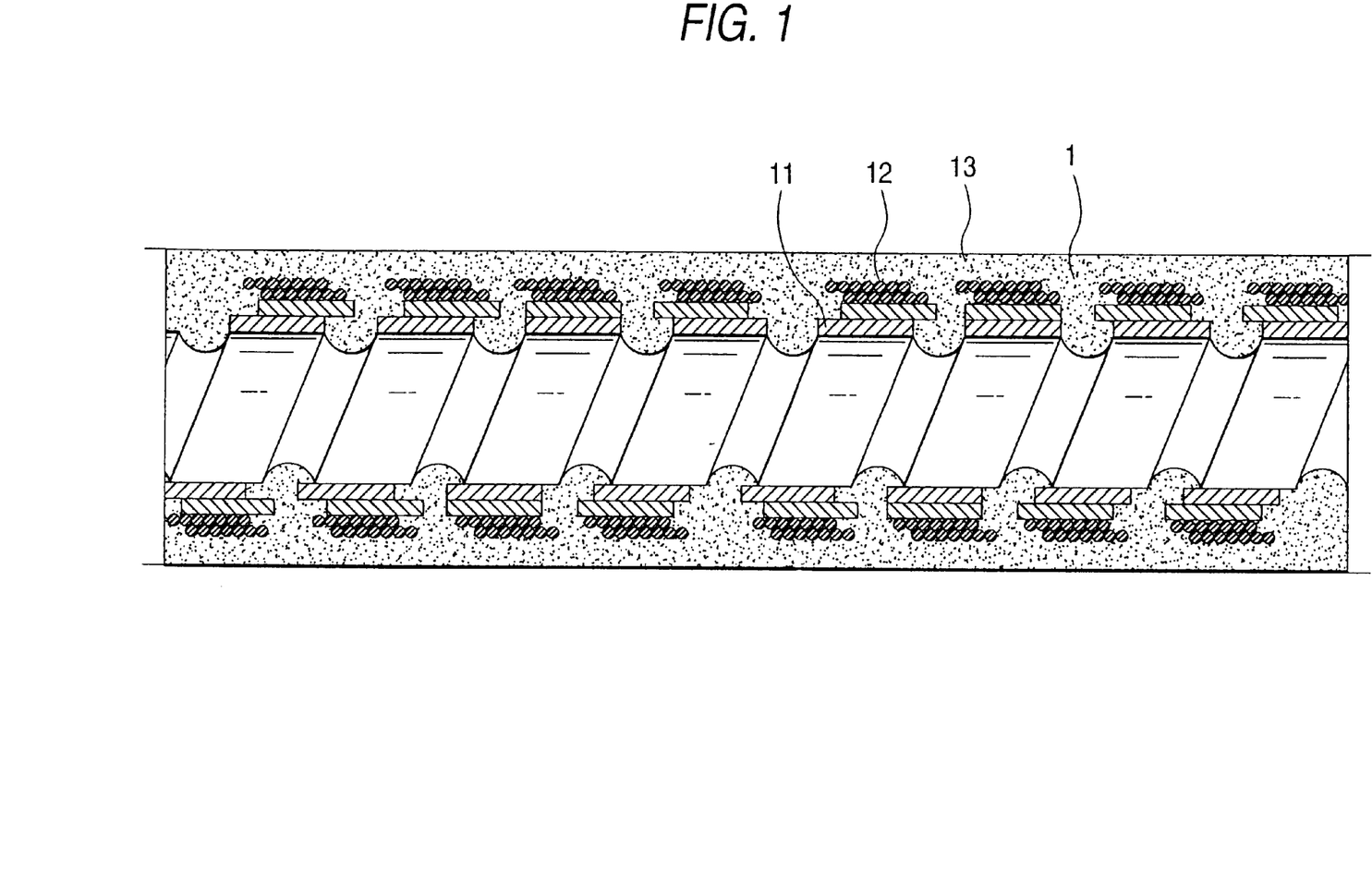
FIG. 1 is a partial longitudinal section of a first flexible tube for an endoscope according to the present invention.

FIG. 1 shows a longitudinal section of an intermediate portion of a flexible tube for an endoscope, which is typically used as a jacket for an inserting part of the endoscope or a light guide cable for connecting a light guide to a light source unit.

As an innermost layer of the flexible tube, a spiral coil 11 is used which is formed by spirally winding a strip of stainless steel or the like having a predetermined diameter, under the condition where gaps are defined between adjacent turns of the spiral coil 11. The spiral coil 11 contains two superposed layers that are wound in different directions. The spiral coil may include only one layer or three or more layers. The spiral coil has edge portions.

The spiral coil 11 is covered with a reticulate tube 12 which is formed by braiding fine stainless steel wires or the like in a tubular form. The reticulate tube 12 may also include one or more layers.

The reticulate tube 12 is covered with a jacket 13 typically made of a thermoplastic synthetic resin such as a polyurethane resin. The jacket 13 is formed by first applying a molten synthetic resin material (jacket material) 1 by an extrusion molding machine onto an outer surface of the reticulate tube 12 and then cooling the applied layer to be cured. The outer surface of the jacket 13 is covered with a chemical resistant coating.

When the jacket material 1 is in a molten state, the jacket material 1 penetrates through openings in the reticulate tube 12 to get into the gaps between the pitches of the spiral coil 11, from which the jacket material moves inward of the spiral coil 1 before curing. Hence, an inner edge of the spiral coil 11 is all covered with the jacket material 1.

Accordingly, the tube enclosing the optical fiber bundle (not shown) passing through the flexible tube makes no direct contact with the edges of the spiral coil 11 but contacts only the jacket material 1 covering the edge thereof.

As a result, even if the flexible tube bends at small radii of curvature in various directions or restores the straight state, the tube covering the optical fiber bundle would not be damaged and, hence, no optical fibers would break.

In order to have the jacket material 1 penetrate until the jacket material 1 reaches the portions of the inner surface of the spiral coil as described above, the pressure being applied to the resin may be increased during extrusion molding or further the resin near the extruding nozzle may be heated.

Figure 2:
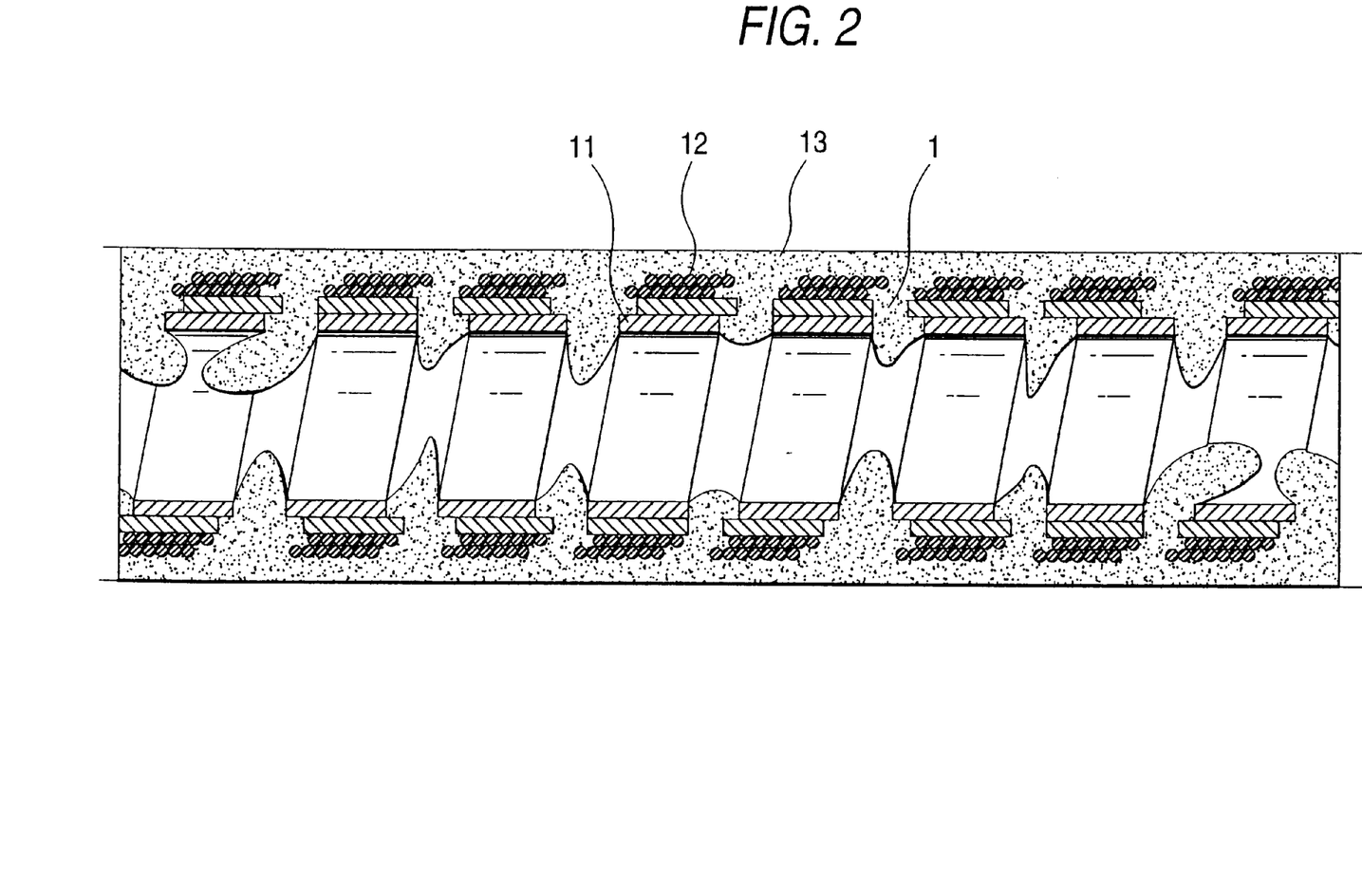
FIG. 2 is a partial longitudinal section of a defective flexible tube for the endoscope.

However, these methods in which the pressure is increased or the resin is heated are simply applied, either excessive or uneven amounts of the jacket material 1 would penetrate through the gaps between the pitches of the spiral coil 1 to get into its interior as shown in FIG. 2. To achieve the uniform penetration shown in FIG. 1, conditions for the extrusion molding have to be set distinctly.

Figure 3:
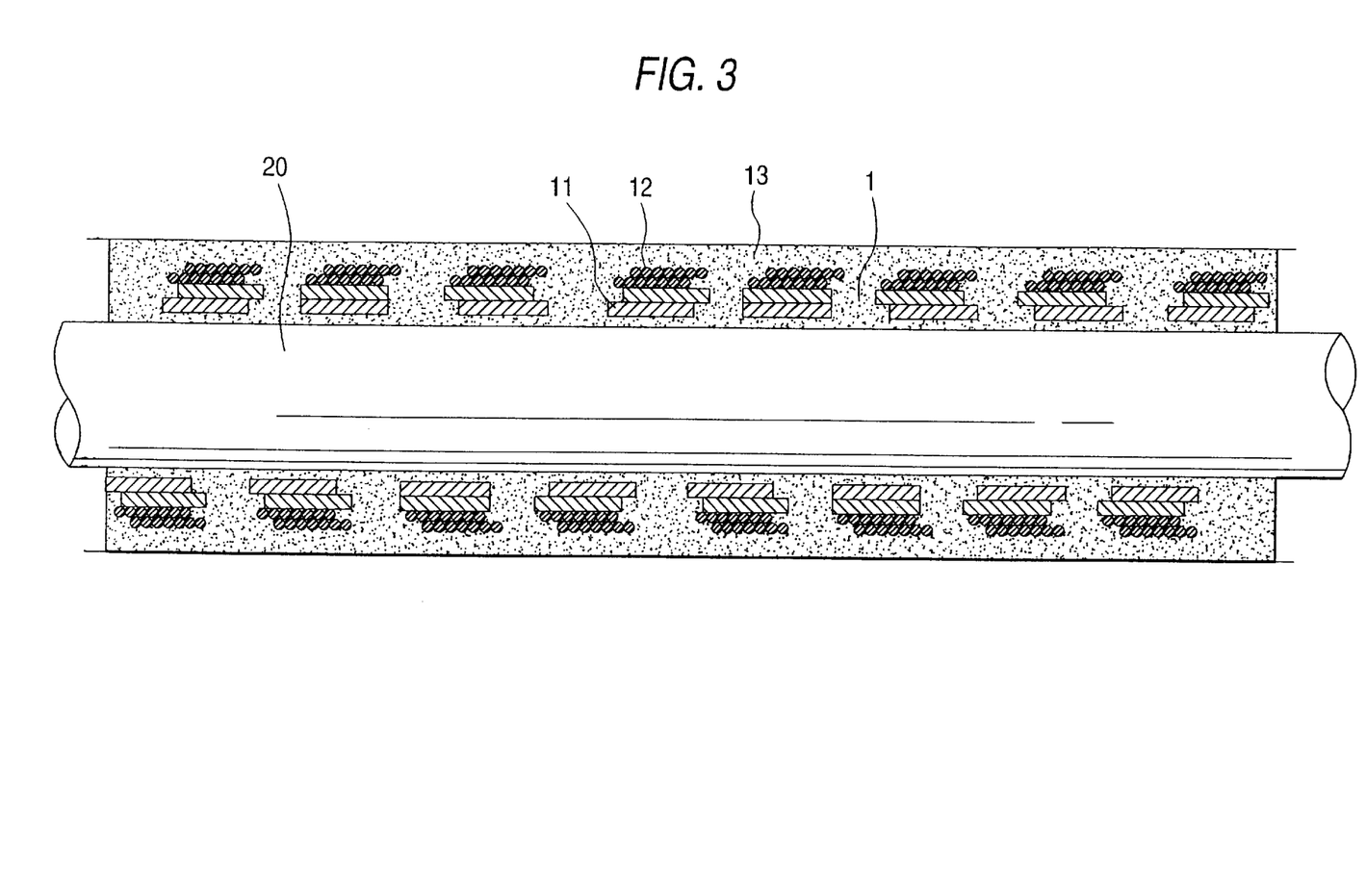
FIG. 3 shows in partial longitudinal section in the case of inserting a mandrel and then applying a jacket material.
Figure 4:
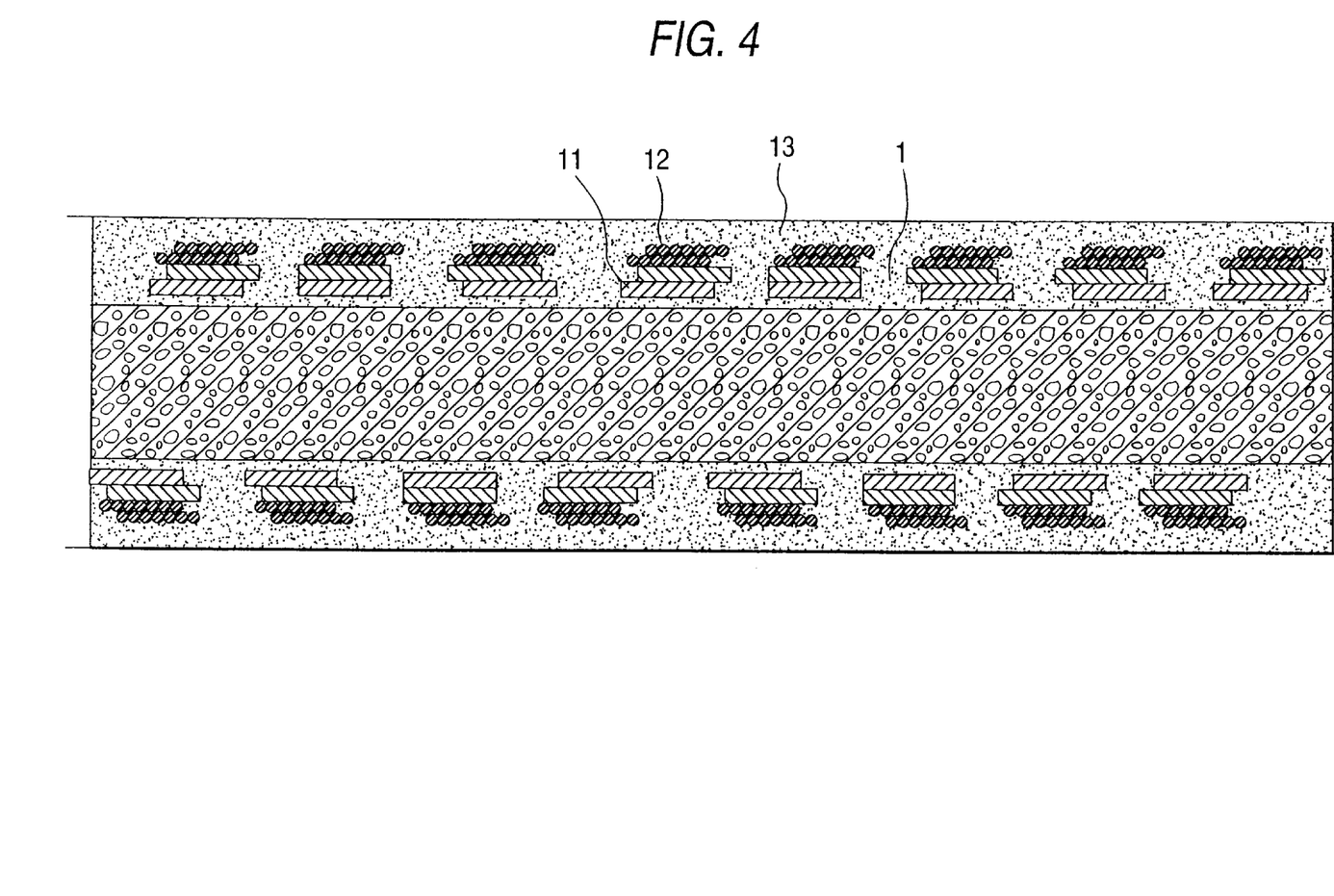
FIG. 4 is a partial longitudinal section of a second flexible tube for the endoscope according to the present invention.

To solve this difficulty, a mandrel 20 as shown in FIG. 3 is loosely inserted through the spiral coil 11 during the extrusion molding and removed after the jacket material 1 cures. Then, the extrusion molding can be accomplished as shown in FIG. 4, where the jacket material 1 has penetrated to portions of the inner surface of the spiral coil 11 to form a uniform thin layer over all of these inner surface. Obviously, a result of the extruding is not influenced by slight variations in molding temperature and pressure.

As a result, the edge of the spiral coil 11 is sufficiently covered with the jacket material 1 to ensure that there would be no damage of the optical fibers resulting from a damage of the tube covering the optical fibers. Moreover, the jacket material 1 provides a strong mechanical connection between the spiral coil 11 and the reticulate tube 12. Hence, the endoscope can be repeatedly used without losing the integrity between the spiral coil 11, reticulate tube 12 and jacket 13 and the initial flexibility of the flexible tube is maintained without suffering from any difficulties such as buckling and wrinkle formation.

The mandrel 20 may be a rod made of metals such as stainless steel. The mandrel may also be made of soft or flexible materials such as plastics and rubbers because they permit the extrusion molding to be performed continuously.

If desired, the surface of members on the side where the jacket material 1 is applied by the extrusion molding (i.e., a tube including the spiral coil 11 covered with the reticulate tube 12) may be subjected to a surface treatment such as coating or plating, primer coating, application of an adhesive or any other suitable treatments that can enhance the bond to the jacket material 1.

In FIG. 4, the jacket material 1 penetrates to the portions of the inner surface of the spiral coil 11 to form a layer that entirely covers its inner surface, so that the finished flexible tube results in not completely flexible but somewhat rigid.

Figure 5:
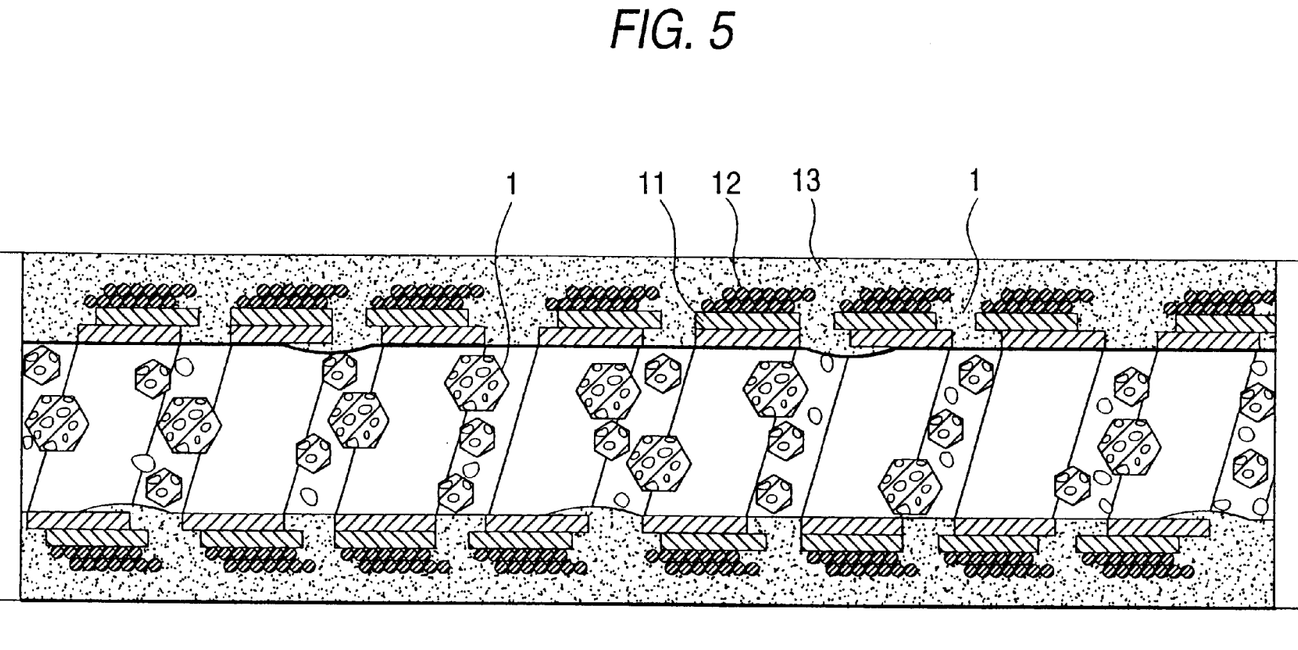
FIG. 5 is a partial longitudinal section of a third flexible tube for the endoscope according to the present invention.

To deal with this difficulty, the penetration of the jacket material 1 may be reduced when performing the extrusion molding using the mandrel 20 so that the jacket material 1 can be penetrates to the portions of the inner surface of the spiral coil 11 and yet the jacket material 1 only partly covers the inner surface of the spiral coil 11 as shown in FIG. 5.

The thus formed flexible tube retains features as well as those in the case where the inner surface of the spiral coil 11 are entirely covered with the jacket material 1 and yet the tube has a proper flexibility.

According to the present invention, the jacket material that is cured after being applied in a molten state is allowed to penetrate through gaps between adjacent layers of the spiral coil as the innermost layer until it reaches the portions of the inner surface of the spiral coil. Therefore, the inner edges of the spiral coil can be covered with the jacket material. Hence, the flexible tube for the endoscope of the present invention permits a repeated use of an endoscope without causing the internally passing optical fiber bundle and the like to be damaged by the inner surface of the innermost spiral coil. If the inner surface of the spiral coil are all or in part covered with the penetration of the jacket material, the bond between the spiral coil and other member is sufficiently enhanced to reduce the variations in flexibility that will occur after repeated use of the endoscope.

What is claimed is:

1. A flexible tube for an endoscope comprising:
   a spiral coil defining gaps between adjacent turns of said spiral coil; and
   a jacket formed by a jacket material and covering at least an outer surface of said spiral coil;
   wherein said jacket material penetrates through said gaps to cover at least edges of said spiral coil, and wherein said spiral coil includes one or more superimposed layers which are covered with one or more layers of a reticulate tube, said reticulate tube being embedded in said jacket material.

2. A flexible tube as claimed in claim 1, wherein the inner surface of said spiral coil is entirely covered with said jacket material.

3. The flexible tube as recited in claim 1, said jacket comprising a thermoplastic synthetic resin.

4. The flexible tube as recited in claim 1, an outer surface of said jacket being covered with a chemical resistant coating.

5. A method of producing a flexible tube for an endoscope comprising:

setting a spiral coil as an innermost layer on a mandrel with a clearance between an outer surface of said mandrel and an inner surface of said spiral coil;

applying a melt of a jacket material onto said spiral coil to penetrate through gaps between adjacent turns of said spiral coil into said clearance;

curing said jacket material; and removing said mandrel.

6. A method as claimed in claim 5, wherein said spiral coil contains one or more superposed layers.

7. A method as claimed in claim 5, further comprising:

covering said spiral coil with one or more layers of a reticulate tube after setting said spiral coil.

8. A method as claimed in claim 5, wherein said jacket material is a thermoplastic synthetic resin and applied with an extrusion molding machine.

9. A method as claimed in claim 5, further comprising:

performing a bond enhancing treatment to said spiral spring and a reticulate tube to which said jacket material is applied before applying said jacket material onto said spiral coil.

10. The method according to claim 9, wherein the bond enhancing treatment comprises one of coating, plating, primer coating and adhesive application.

11. The method according to claim 5, further comprising:

performing a bond enhancing treatment on a member to which said jacket material is applied, before applying said jacket material onto said spiral coil.

12. The method according to claim 11, wherein the bond enhancing treatment comprises one of coating, plating primer coating and adhesive application.

* * * * *